(12) United States Patent
Dekeyser et al.

(10) Patent No.: US 6,180,126 B1
(45) Date of Patent: Jan. 30, 2001

(54) PESTICIDAL THIADIAZINE COMPOUNDS

(75) Inventors: Mark Achiel Dekeyser, Waterloo (CA); Paul Thomas McDonald, Middlebury, CT (US)

(73) Assignees: Uniroyal Chemical Company, Inc., Middlebury, CT (US); Uniroyal Chemical Co./Uniroyal Chemical CIE., Elmira (CA)

( * ) Notice: Under 35 U.S.C. 154(b), the term of this patent shall be extended for 0 days.

(21) Appl. No.: 09/228,306

(22) Filed: Jan. 12, 1999

Related U.S. Application Data

(62) Division of application No. 08/806,351, filed on Feb. 26, 1997, now abandoned.

(51) Int. Cl.[7] .............................. A01N 25/00; A01N 43/88
(52) U.S. Cl. .............................. 424/405; 514/222.5; 548/8
(58) Field of Search ........................ 424/405; 514/222.5; 548/8

(56) References Cited

U.S. PATENT DOCUMENTS

| | | | |
|---|---|---|---|
| 3,420,826 | * | 1/1969 | Trepanier ........................... 260/244 |
| 5,536,720 | * | 7/1996 | Dekeyser et al. ................. 574/229.2 |

OTHER PUBLICATIONS

Trepanier et al 5,6–dihydro 4m–1,3,4–oxadiazines—J. Med. Chem. 9 : 753–758, 1966.*
Schulzo et al J. Prakt. Chem. 36(3–4) 138–47, 1967.*

* cited by examiner

Primary Examiner—Neil S. Levy
(74) Attorney, Agent, or Firm—Daniel Reitenbach

(57) ABSTRACT

Insecticidal and miticidal compounds of the formula

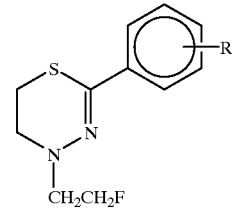

wherein R is hydrogen, halogen, nitro, $C_1$–$C_8$ alkyl, $C_1$–$C_8$ alkoxyl, or $C_1$–$C_6$ haloalkyl,
compositions comprising these compounds, and methods for their use.

6 Claims, No Drawings

PESTICIDAL THIADIAZINE COMPOUNDS

This is a division of U.S. patent application Ser. No. 08/806,351, filed on Feb. 26, 1997.

FIELD OF THE INVENTION

This invention relates to pesticidal thiadiazine derivatives. More particularly, this invention relates to thiadiazine derivatives which exhibit activity as insecticides and as miticides. This invention also relates to insecticidal and miticidal compositions comprising the thiadiazine derivatives as well as to methods of controlling insects and acarids employing such compounds or compositions.

BACKGROUND OF THE INVENTION

Destruction of crops by insects and acarids presents a serious problem to agriculture. A wide variety of field crops are in need of protection from acarids and insects. Particularly difficult types of acarids and insects to control are those which, at one or more stages of their life, inhabit the soil and cause destruction to the roots of plants. Accordingly, the development of insecticides and miticides which are effective as ovicides, larvicides, and adulticides is desirable. Certain oxadiazine compounds have been described as useful as pesticides and as pharmaceutical agents. For example, U.S. Pat. No. 5,536,720 describes substituted 2-phenyl-1,3,4-oxadiazine-4-carbamide compounds useful as insecticides and acaricides. Trepanier et al, J. Med. Chem 9: 753–758 (1966) describe certain 2-substituted 4H-1,3,4-oxadiazines useful as anticonvulsants in mice. U.S. Pat. No. 3,420,826 describes certain 2,4,6-substituted 4H-1,3,4-oxadiazines, useful as sedatives, anticonvulsants, and as pesticides against nematodes, plants, and fungi. U.S. Pat. No. 3,420,825 describes methods for producing certain 2,4,6-substituted 4H-1,3,4-oxadiazines.

It is a purpose of this invention to provide novel thiadiazine derivatives useful as insecticides and miticides.

SUMMARY OF THE INVENTION

This invention relates to a compound of the formula

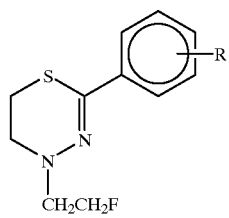

(I)

wherein R is hydrogen, halogen, nitro, $C_1$–$C_8$ alkyl, $C_1$–$C_8$ alkoxyl, or $C_1$–$C_8$ haloalkyl. The compounds of this invention useful as plant protecting agents for the control of mite and insect pests.

The present invention also relates to a pesticidal composition comprising: a) an effective amount of a compound of formula I; and b) a suitable carrier.

The present invention further relates to a method for controlling insects or acarids which comprises applying an effective amount of the compound of formula I to the locus to be protected.

DETAILED DESCRIPTION OF THE INVENTION

It is preferred that the compound of formula I has the formula

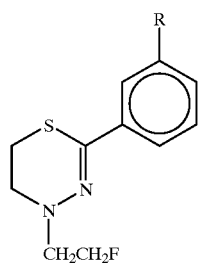

(IA)

or

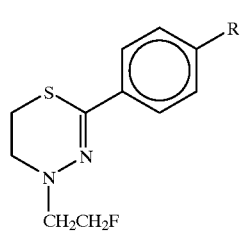

(IB)

wherein R is as defined above.

Preferably, in the compound of formula I (and accordingly, in the compounds of formulas IA and IB), R is hydrogen, halogen, nitro, $C_1$–$C_4$ alkyl, $C_1$–$C_4$ alkoxyl, or $C_1$–$C_4$ trihaloalkyl. More preferably, R is hydrogen, methyl, ethyl, methoxy, ethoxy, trifluoromethyl, bromine, fluorine, iodine, or nitro.

The compounds of the present invention can be prepared by reacting a hydrazide of formula A below, wherein R is as defined above, and bromofluoroethane, in the presence of a base such as potassium or sodium hydroxide. The resulting intermediate of formula B is then reacted with Lawesson's reagent to produce the compound of formula I. Lawesson's reagent is [2,4-bis(4-methoxyphenyl)-1,3-dithia-2,4-diphosphetane-2,4-disulfide (available from Aldrich Chemical Company).

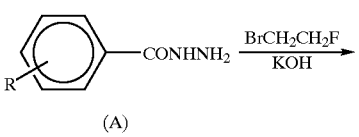

(A)

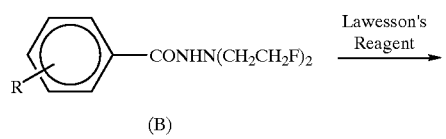

(B)

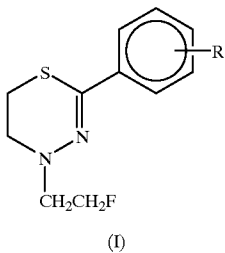

The compositions of the present invention can be prepared by formulating one or more compounds of the present invention with a suitable carrier.

Suitable liquid carriers can comprise water, alcohols, ketones, phenols, toluene and xylenes. In such formulations, additives conventionally employed in the art can be utilized, such as one or more surface active agents and/or inert diluents, to facilitate handling and application of the resulting insecticidal composition.

Alternatively, the compounds of this invention can be applied as a liquid or in sprays when utilized in a liquid carrier, such as a solution comprising a compatible solvent such as acetone, benzene, toluene or kerosene, or a dispersion comprising a suitable non-solvent medium such as water.

The compositions of this invention can alternatively comprise solid carriers taking the form of dusts, granules, wettable powders, pastes, aerosols, emulsions, emulsifiable concentrates, and water-soluble solids. For example, the compounds of this invention can be applied as dusts when admixed with or absorbed onto powdered solid carriers, such as mineral silicates, talc, pyrophyllite and clays, together with a surface-active dispersing agent so that a wettable powder is obtained which then is applied directly to the loci to be treated. Alternatively, the powdered solid carrier containing the compound admixed therewith, can be dispersed in water to form a suspension for application in such form.

Granular formulations of the compounds are preferred for field treatment and are suitable for application by broadcasting, side dressing, soil incorporation or seed treatment, and are suitably prepared using a granular or pelletized form of carrier such as granular clays, vermiculite, charcoal or corn cobs. The compound of this invention is dissolved in a solvent and sprayed onto an inert mineral carrier such as attapulgite granules (10–100 mesh), and the solvent is then evaporated. Such granular compositions can contain from 2–25% of a compound of this invention, based on carrier plus compound, preferably, 3–15%. In addition, the compounds of this invention can also be incorporated into a polymeric carrier such as polyethylene, polypropylene, butadiene-styrene, styrene-acryonitrile resins, polyamides, poly(vinyl acetates), and the like. When encapsulated, the compound of this invention can advantageously be released over an even longer time period, extending its effectiveness further than when used in non-encapsulated form.

Another method of applying the compound of this invention to the loci to be treated is by aerosol treatment, for which the compound can be dissolved in an aerosol carrier which is a liquid under pressure but which is a gas at ordinary temperature (e.g., 20° C.) and atmospheric pressure. Aerosol formulations can also be prepared by first dissolving the compound in a less volatile solvent and then admixing the resulting solution with a highly volatile liquid aerosol carrier.

For treatment of plants (such term including plant parts), the compounds of the invention preferably are applied in aqueous emulsions containing a surface-active dispersing agent which can be non-ionic, cationic or anionic. Suitable surface-active agents are well known in the art, such as those disclosed in U.S. Pat. No. 2,547,724 (columns 3 and 4). The compounds of this invention can be mixed with such surface-active dispersing agents, with or without an organic solvent, as concentrates for the subsequent addition of water, to yield aqueous suspensions of the compounds at desired concentration levels.

In addition, the compounds can be employed with carriers which themselves are pesticidally active, such as insecticides, acaricides, fungicides or bactericides.

It will be understood that the effective amount of a compound in a given formulation will vary depending, e.g., upon the specific pest to be combated, as well as upon the specific chemical composition and formulation of the compound being employed, the method of applying the compound/formulation and the locus of treatment. Generally, however, the effective amount of the compound of this invention can range from about 0.1 to about 95 percent by weight. Spray dilutions can be as low as a few parts per million, while at the opposite extreme, full strength concentrates of the compound can be usefully applied by ultra low volume techniques. When plants constitute the loci of treatment, concentration per unit area can range between about 0.01 and about 50 pounds per acre, with concentrations of between about 0.1 and about 10 pounds per acre preferably being employed for crops such as corn, tobacco, rice and the like.

To combat insects and mites, sprays of the compounds can be applied to any suitable locus, such as to the insects or mites directly and/or to plants upon which they feed or nest. The compositions of this invention can also be applied to the soil or other medium in which the pests are present. The specific methods of application of the compounds and compositions of this invention, as well as the selection and concentration of these compounds, will vary depending upon such circumstances as crops to be protected, geographic area, climate, topography, plant tolerance, etc.

The compounds of the invention are particularly useful as insecticides and acaricides, for foliar and/or soil application. The compounds are particularly effective for controlling insects, such as corn rootworm, which live in the soil during one or more phases of their lives, by means of soil application.

The following examples are provided to illustrate the present invention.

EXAMPLES

Example 1

Preparation of 2-(4-bromophenyl)-4-(2-fluoroethyl)-4H-1,3,4-thiadiazine hydrochloride (Compound No. 3)

To 25 g of 4-bromobenzoic hydrazide suspended in 50 ml of ethanol was added 28 g of 1-bromo-2-fluoroethane followed by a solution of 15 g of potassium hydroxide dissolved in 25 ml of water, to produce a reaction mixture. The reaction mixture was stirred for 4 hours. 200 ml of water was then added to the reaction mixture. The reaction mixture was then extracted with 500 ml of dichloromethane. The dichloromethane portion was separated, dried over anhydrous sodium sulfate and then reduced in volume. The remaining solid was washed with hexane and identified by NMR as 2,2-bis(2-fluoroethyl)-hydrazide of 4-bromobenzoic acid. This material was added to 100 ml of p-xylene and treated with 29 g of Lawesson's reagent, to produce a second reaction mixture. The second reaction mixture was refluxed for 1 hour, cooled to room temperature, and filtered. The filtrate was treated with gaseous hydrochloric acid until no further solid precipitated, and then filtered, to produce 2-(4-bromophenyl)-4-(2-fluoroethyl)-4H-1,3,4-thiadiazine hydrochloride as a yellow solid (8 g, mp 116–117° C.).

The other compounds listed in Table 1 below were prepared using the procedure described above in Example 1. Each compound is characterized by its NMR data.

TABLE 1

(I)

structure: phenyl ring with R substituent, connected to thiadiazine ring with S, N-N, with CH$_2$CH$_2$F on N

| No | R | NMR data (PPM) in DMSO |
|---|---|---|
| 1 | 4-I | m(5) 3.1–3.4, t(1) 4.3, t(1) 5.1, m(4) 7.3–7.8 |
| 2 | 4-C$_2$H$_5$ | t(3) 1.0–1.3, 9(2) 2.4–2–8, m(5) 3.1–3.4, t(1) 3.7, t(1) 4.3, t(1) 5.1, m(4) 7.0–7.8 |
| 3 | 4-Br | m(5) 3.1–3.4, t(1) 3.7, t(1) 4.3, t(1) 5.1, s(4) 7.5 |
| 4 | H | m(5) 3.1–3.5, t(1) 3.7, t(1) 4.4, t(1) 5.2, m(5) 7.3–7.8 |
| 5 | 3–NO$_2$ | m(6) 3.1–3.8, t(1) 4.4, t(1) 5.1, m(4) 7.6–8.3 |
| 6 | 4-F | m(5) 3.1–3.5, t(1) 3.7, t(1) 4.4, t (1) 5.2, m(4) 7.1–7.8 |
| 7 | 4-CF$_3$ | s(9) 1.2, m(5) 3.1–3.4, s(1) 3.6, s(1) 4.3, s(1) 5.1 |
| 8 | 4-OC$_2$H$_5$ | t(3) 1.0–1.3, m(6) 2.9–3.5, m(2) 3.6–3.9, m(2) 4.1–5.1, m(4) 6.8–7.6 |

Preparation of Formulations

The remaining examples relate to the insecticidal and miticidal use of the compounds of this invention. In all these examples, a 3000 ppm stock solution of the compounds was prepared by dissolving 0.24 gram of each compound to be tested in 8 ml of acetone and adding 72 ml of distilled water plus 3 drops of ethoxylated sorbitan monolaurate, a wetting agent. This stock solution was used in the remaining examples demonstrating the insecticidal and miticidal use of representative compounds of this invention. For each example that follows, this stock solution was used and the specificized dilutions made. All the tests discussed below, which involved treatment with compounds of this invention were always repeated with controls, in which the active compound was not provided, to permit a comparison upon which the percent control was calculated.

Example 2
Southern Corn Rootworm Test

The stock solution of 3000 ppm was diluted to 100 ppm (test solution). For each compound, 2.5 ml of the test solution was pipetted onto a filter paper (Whatman #3) at the bottom of a 100 mm petri dish. Two corn seedlings were soaked in the 100 ppm solution for 1 hour and transferred to the petri dish containing the same test solution. After 24 hours, each dish was loaded with 5 second instar larvae of Southern Corn Rootworm (*Diabrotica undecimpunctata*). After five days, the number of live larvae was noted and the percent control, corrected by Abbott's formula [see J. Economic Entomology 18: 265–267 (1925)] was calculated.

The results of the testing of Southern Corn Rootworm (CR) are presented below in Table 2.

Example 3
Mite Adulticide and Mite Ovicide Tests

One day before treatment of cowpea primary leaves with the test solutions, a "FIG. 8" configuration of tree tanglefoot was applied to each of two cowpea primary leaves, one from each of two plants in a pot. In each figure, the circle nearer the stem was designated for the mite ovicide test and the circle further from the stem was designated for the mite adulticide test.

Groups of adult mites (*Tetranychus urticae* Koch) were transferred into ovicide circles one day before treatment and the females were allowed to deposit eggs until one hour before treatment, at which point all the adults were removed. The plants were then sprayed to run off with a 1000 ppm solution diluted from the 3000 ppm stock solution.

One day following treatment of the plants with the test solution, groups of approximately 25 adult mites were transferred into the adulticide rings. Five days later these rings were examined for live mites remaining on the leaves. The percent control was estimated based on the number of mites surviving on the control plants.

Nine days following treatment the ovicide rings were examined for unhatched eggs and living immature mites. The percent control was estimated based on the number of unhatched eggs.

Results of the mite adulticide (MI) and ovicide (MIOV) tests are presented below in Table 2.

Example 4
Rice Planthopper Foliar Test

The stock solution of 3000 ppm was diluted to 1000 ppm. Using a spray atomizer, each test solution was sprayed onto a separate pot containing approximately 20 Mars variety rice seedlings. One day after spraying, the plants were covered with a tubular cage and twenty adult rice delphacides (*Sogatodes orizicola*), were transferred into each cage. Five days after transferring, counts were made of the surviving planthoppers in each pot and percent control was estimated.

Results of the rice planthopper (RHP) tests are presented in Table 2 below.

Example 5

Tobacco Budworm Test

The undiluted 3000 ppm stock solution (test solution) for each compound was used for this test. 0.2 ml of each test solution was pipetted onto the surface of each of 5 diet cells, allowed to spread over the surfaces and air dried for two hours. Then a second instar larva of Tobacco Budworm (*Heliothis virescens*) was introduced into each cell. After 14 days, the number of living larvae was determined for each test solution and percent control, corrected by Abbott's formula, was calculated.

The results of the testing of tobacco budworms (TB) are given in Table 2 below.

Example 6

Tobacco Budworm Ovicide Test

A solution of 1000 ppm was prepared by dissolving 0.015 g of each compound to be tested in 2 ml of acetone and adding 13 ml of distilled water plus 1 drop of ethoxylated sorbitan monolaurate. Cheesecloth on which budworms had oviposited eggs 1–2 days before treatment, was cut into pieces containing 40–80 eggs. Each piece was immersed for 1 minute in one test solution. After 5 days, the number of hatched and unhatched eggs on each piece was counted and an adjusted percent control was determined.

The results of the Tobacco Budworm Ovicide Test (TBOV) is presented in Table 2 below.

TABLE 2

| | | | Percent Control | | | |
|---|---|---|---|---|---|---|
| Cmpd. | CR | MI | MIOV | RPH | TB | TBOV |
| 1 | 0 | 70 | 100 | 0 | 76 | 100 |
| 2 | 16 | 0 | 100 | 0 | 23 | 100 |
| 3 | 0 | 40 | 100 | 0 | 80 | 100 |
| 4 | 60 | 0 | 100 | 0 | 100 | 100 |
| 5 | 59 | 0 | 100 | 95 | 100 | 94 |
| 6 | 60 | 0 | 100 | 0 | 100 | 100 |
| 7 | 100 | 0 | 100 | 0 | 100 | 99 |
| 8 | 0 | 0 | 100 | 0 | 100 | 100 |

What is claimed is:

1. An insecticidal or miticidal compound of the formula

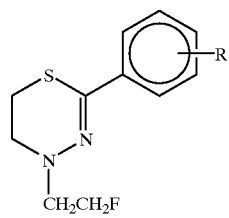

(I)

wherein R is hydrogen, halogen, nitro, $C_1$–$C_8$ alkyl, $C_1$–$C_8$ alkoxyl, or $C_1$–$C_6$ haloalkyl.

2. A compound as recited in claim 1 wherein R is hydrogen, halogen, nitro, $C_1$–$C_4$ alkyl, $C_1$–$C_4$ alkoxyl, or $C_1$–$C_4$ trihaloalkyl.

3. A compound as recited in claim 2 wherein R is hydrogen, methyl, ethyl, methoxy, ethoxy, trifluoromethyl, bromine, fluorine, iodine, or nitro.

4. A compound as recited in claim 1 having the formula

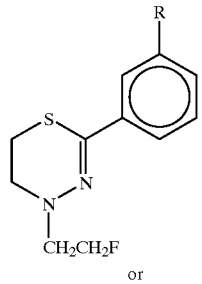

(IA)

or

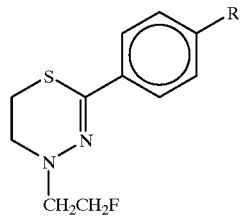

(IB)

5. A compound as recited in claim 4 wherein R is hydrogen, halogen, nitro, $C_1$–$C_4$ alkyl, $C_1$–$C_4$ alkoxyl, or $C_1$–$C_4$ trihaloalkyl.

6. A compound as recited in claim 5 wherein R is hydrogen, methyl, ethyl, methoxy, ethoxy, trifluoromethyl, bromine, fluorine, iodine, or nitro.

* * * * *